United States Patent
Hebrank

(10) Patent No.: US 10,119,950 B2
(45) Date of Patent: Nov. 6, 2018

(54) EGG IDENTIFICATION SYSTEM, AND ASSOCIATED METHOD

(71) Applicant: Zoetis Services LLC, Parsippany, NJ (US)

(72) Inventor: John Hilbert Hebrank, Durham, NC (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 15/471,016

(22) Filed: Mar. 28, 2017

(65) Prior Publication Data

US 2017/0284989 A1    Oct. 5, 2017

Related U.S. Application Data

(60) Provisional application No. 62/314,558, filed on Mar. 29, 2016.

(51) Int. Cl.
*G01N 21/53* (2006.01)
*G01N 33/08* (2006.01)
(Continued)

(52) U.S. Cl.
CPC .......... *G01N 33/085* (2013.01); *G01N 21/31* (2013.01); *G01N 21/59* (2013.01);
(Continued)

(58) Field of Classification Search
CPC .... G01N 33/085; G01N 21/359; G01N 21/49; G01N 21/3563; G01N 21/474; G01N 33/08; G01N 2021/845; G01N 21/5907; G01N 21/8806; G01N 2223/618; G01N 2223/643; G01N 23/04
See application file for complete search history.

(56) References Cited

U.S. PATENT DOCUMENTS 5,646,722 A * 7/1997 van der Schoot ... G01N 33/085
356/53
5,900,929 A 5/1999 Hebrank et al.
(Continued)

FOREIGN PATENT DOCUMENTS

EP 0715168 A1 6/1996
EP 2845477 A1 3/2015

OTHER PUBLICATIONS

International Search Report and Written Opinion, International Application No. PCT/US2017/024427, dated Jun. 7, 2017.

*Primary Examiner* — Michael P Stafira
(74) *Attorney, Agent, or Firm* — Scott C. Mayhew

(57) ABSTRACT

An egg identification system for determining egg viability is provided. Such a system includes an emitter assembly for emitting electromagnetic radiation toward a plurality of eggs positioned proximate thereto. A detector assembly is positioned proximate to the emitter assembly. The detector assembly has a plurality of detectors fixedly positioned with respect to the emitter assembly and configured to detect electromagnetic radiation transmitted through the eggs. An optical shielding assembly is configured to move with respect to the detectors. A processor is in communication with detector assembly and is configured to determine viability of the eggs using the detected electromagnetic radiation. An associated method is also provided.

8 Claims, 5 Drawing Sheets

(51) Int. Cl.
*G01N 21/59* (2006.01)
*G01N 21/31* (2006.01)

(52) U.S. Cl.
CPC . *G01N 2201/064* (2013.01); *G01N 2201/068* (2013.01); *H05K 999/99* (2013.01)

(56) References Cited

U.S. PATENT DOCUMENTS

| | | |
|---|---|---|
| 6,750,954 B2 * | 6/2004 | Hebrank ................ A01K 43/00 356/53 |
| 2004/0107912 A1 | 6/2004 | Hebrank |
| 2007/0125305 A1 | 6/2007 | Reeves et al. |
| 2009/0091743 A1 | 4/2009 | Hebrank et al. |
| 2015/0308963 A1 * | 10/2015 | Nambu ................ G01N 33/085 356/53 |

* cited by examiner

EGG IDENTIFICATION SYSTEM, AND ASSOCIATED METHOD

CROSS REFERENCE TO RELATED APPLICATION

This application claims the benefit of U.S. Provisional Patent Application No. 62/314,558, filed Mar. 29, 2016, which is expressly incorporated herein by reference in its entirety.

TECHNICAL FIELD

The present disclosure generally relates to egg processing devices and systems. More particularly, the present disclosure relates to a system for identifying an egg as containing a viable or non-viable embryo, and an associated method.

BACKGROUND

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with eggs, although egg shells appear opaque under most lighting conditions, they are in reality somewhat translucent, and when placed in front of direct light, the contents of the egg can be observed.

Eggs which are to be hatched to live poultry are typically candled during embryonic development to identify clear (i.e., infertile), rotted, and dead eggs (collectively referred to herein as "non-live eggs"). Non-live eggs (also referred to as non-viable eggs) are removed from incubation to increase available incubator space and also reduce the risk of bio-contamination. In many instances it is desirable to introduce a substance, via in ovo injection, into a live egg (also referred to as a viable egg) prior to hatch. Injections of various substances into avian eggs are employed in the commercial poultry industry to decrease post-hatch mortality rates or increase the growth rates of the hatched bird. Examples of substances that have been used for, or proposed for, in ovo injection include vaccines, antibiotics and vitamins. Due to the number of non-live eggs encountered in commercial poultry production, the use of automated methods for in ovo injection, and the cost of treatment substances, an automated process for identifying live eggs and selectively injecting only live eggs is desirable.

An egg may be a "live" egg, meaning that it has a viable embryo. FIG. 1 illustrates a live poultry egg 1 at about day one of incubation. FIG. 2 illustrates the live egg 1 at about day eleven of incubation. The egg 1 has a somewhat narrow end in the vicinity represented at 10 as well as an oppositely disposed broadened or blunt end portion in the vicinity shown at 20. In FIG. 1, an embryo 2 is represented atop the yolk 3. The egg 1 contains an air cell 4 adjacent the broadened end 20. As illustrated in FIG. 2, the wings 5, legs 6, and beak 7 of a baby chick have developed.

An egg may be a "clear" or "infertile" egg, meaning that it does not have an embryo. More particularly, a "clear" egg is an infertile egg that has not rotted. An egg may be an "early dead" egg, meaning that it has an embryo which died at about one to five days old. An egg may be a "mid-dead" egg, meaning that it has an embryo which died at about five to fifteen days old. An egg may be a "late-dead" egg, meaning that it has an embryo which died at about fifteen to eighteen days old.

An egg may be a "rotted" egg, meaning that the egg includes a rotted infertile yolk (for example, as a result of a crack in the egg's shell) or, alternatively, a rotted, dead embryo. While an "early dead," "mid-dead" or "late-dead egg" may be a rotted egg, those terms as used herein refer to such eggs which have not rotted. Clear, early-dead, mid-dead, late-dead, and rotted eggs may also be categorized as "non-live" eggs because they do not include a living embryo.

There are other applications where it is important to be able to distinguish between live (viable) and non-live (non-viable) eggs. One of these applications is the cultivation and harvesting of vaccines via live eggs (referred to as "vaccine production eggs"). For example, human flu vaccine production is accomplished by injecting seed virus into a chicken egg at about day eleven of embryonic development (Day-11 egg), allowing the virus to grow for about two days, euthanizing the embryo by cooling the egg, and then harvesting the agnostic fluid from the egg. Typically, eggs are candled before injection of a seed virus to remove non-live eggs. Vaccine production eggs may be candled one or more days prior to injection of a seed virus therein. Identification of live eggs in vaccine production is important because it is desirable to prevent seed vaccine from being wasted in non-live eggs and to reduce costs associated with transporting and disposing of non-live eggs.

Some previous candling apparatuses have employed opacity identification systems in which a plurality of light sources and corresponding light detectors are mounted in an array, and wherein eggs are passed on an egg carrier between the light sources and the light detectors. Unfortunately, such conventional candling techniques may have somewhat limited accuracy due to different categories of eggs having similar optical densities (e.g., live and rotted) resulting in similar levels of transmitted light. Light opacity identification systems can operate to meet 40,000 to 100,000 eggs per hour requirements and successfully identify clear eggs from a stream of eggs. However, some eggs identified as being live may in fact be non-live (e.g., rotted eggs, mid and late dead eggs).

Other previous candling apparatuses have employed embryo heartbeat detection capable of detecting live and non-live eggs. However, these systems have several drawbacks for high throughput applications. First, the throughput parameter is slowed down because the eggs must be sensed for several seconds to detect the faint heartbeat. Second, mechanical vibration or mechanical shock to the machine frame may create false heartbeat signals in nonlive eggs. Third, eggs that are very warm or very cool may have fast, irregular or very slow heartbeats so that live eggs are classified as nonlive.

Accordingly, it would be desirable to provide a candling apparatus implementing a detection system capable of accurately distinguishing live and non-live eggs without stopping movement of the egg carriers through the candling apparatus. Furthermore, it would be desirable to provide an associated method that would facilitate detection of live eggs in a high throughput and accurate manner.

BRIEF SUMMARY

The above and other needs are met by aspects of the present disclosure which, according to one aspect, provides an egg identification system. The system includes an emitter assembly configured to emit electromagnetic radiation toward a plurality of eggs positioned proximate thereto. A detector assembly is positioned proximate to the emitter assembly. The detector assembly has a plurality of detectors fixedly positioned with respect to the emitter assembly and configured to detect electromagnetic radiation transmitted through the eggs. An optical shielding assembly is configured to move with respect to the detectors and to provide optical shielding for detection of the electromagnetic radiation transmitted through the eggs. A processor is in communication with detector assembly and configured to determine viability of the eggs using the detected electromagnetic radiation.

Another aspect provides a method of classifying an egg. The method comprises conveying a plurality of eggs through an egg identification system having an emitter assembly and a detector assembly. The detector assembly has a plurality of detectors fixedly positioned with respect to the emitter assembly and configured to detect electromagnetic radiation transmitted through the eggs. The method further comprises emitting electromagnetic radiation via the emitter assembly toward the eggs. The method further comprises moving an optical shielding assembly in relation to the detectors so as to provide optical shielding for detection of the electromagnetic radiation transmitted through the eggs. The method further comprises detecting electromagnetic radiation transmitted through the eggs with the detectors, and generating an output signal corresponding to intensity of electromagnetic radiation from the emitter assembly transmitted through a respective egg.

Thus, various aspects of the present disclosure provide advantages, as otherwise detailed herein.

BRIEF DESCRIPTION OF THE DRAWINGS

Figure 1:
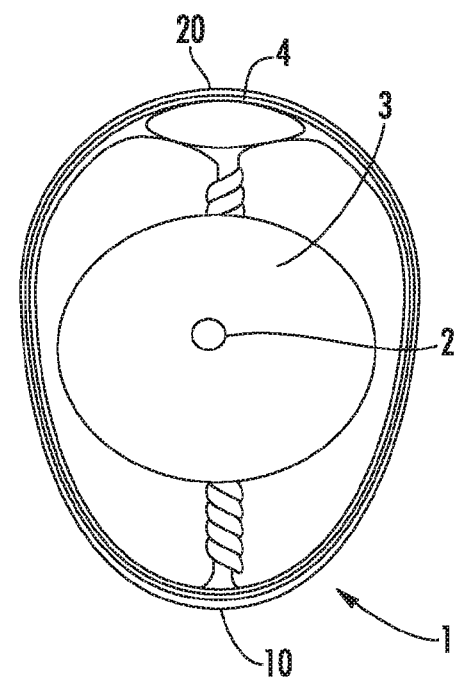
Figure 2:
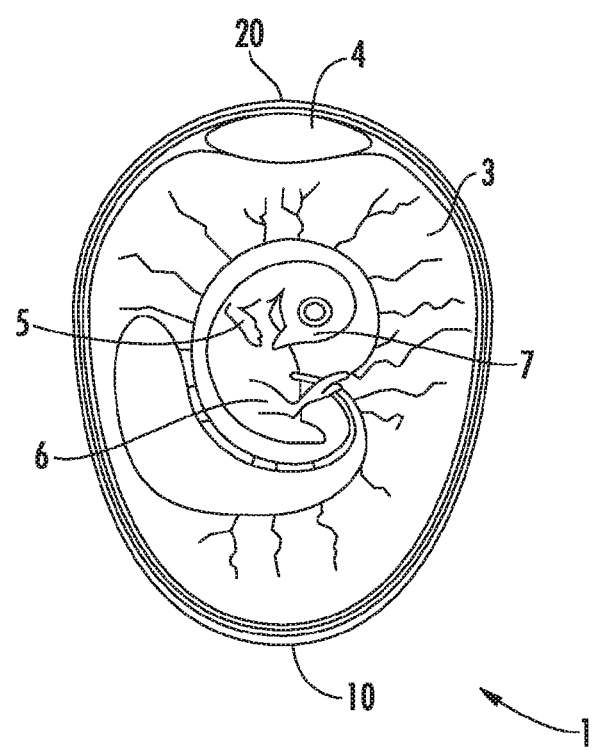
Figure 3:
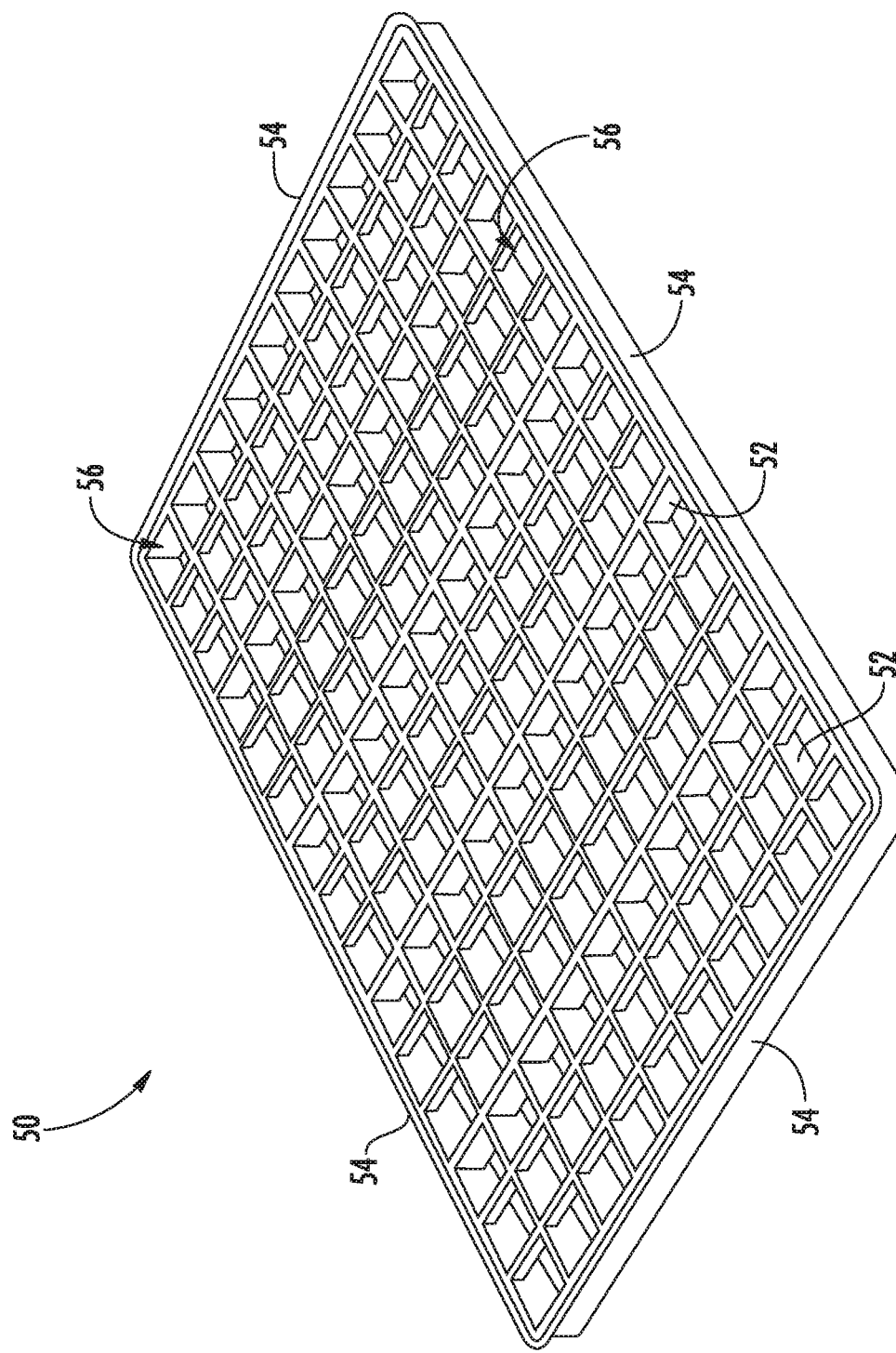
Figure 4:
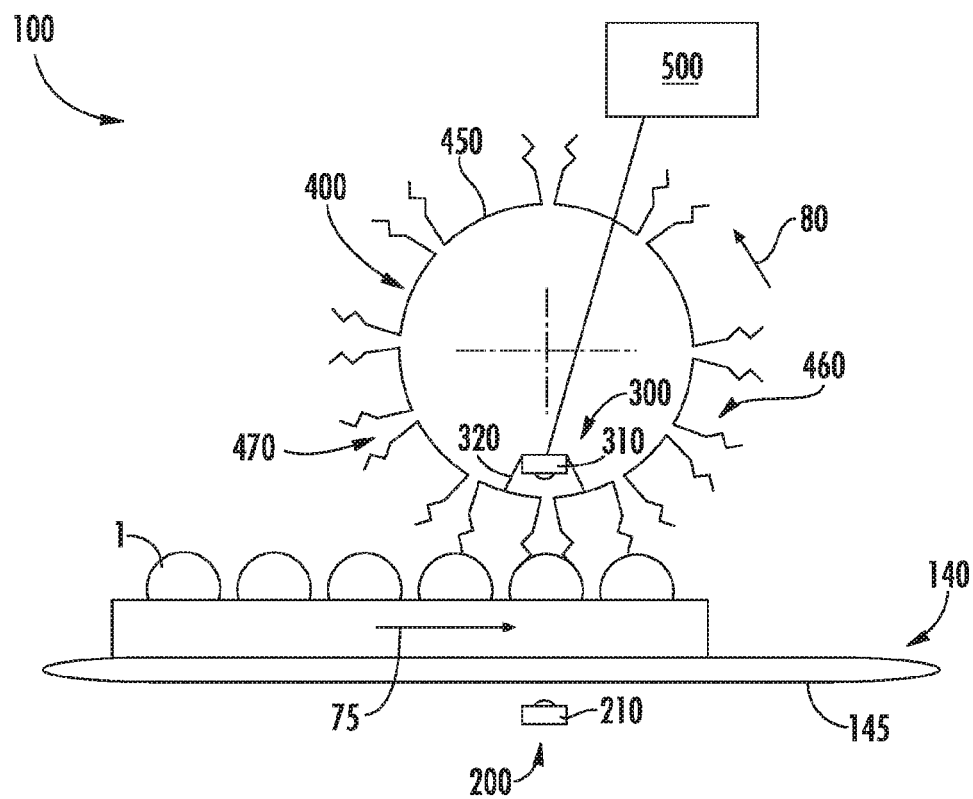
Figure 5:
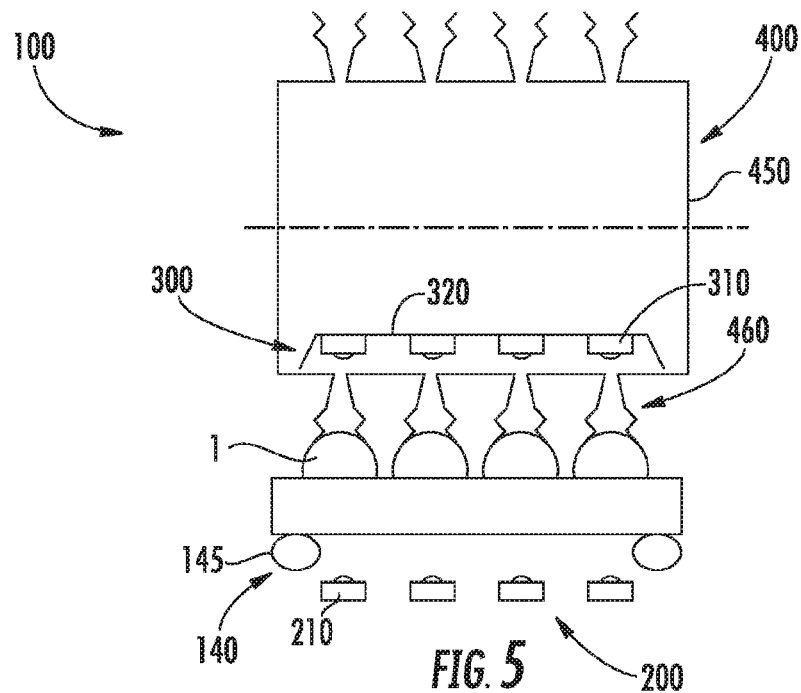
Figure 6:
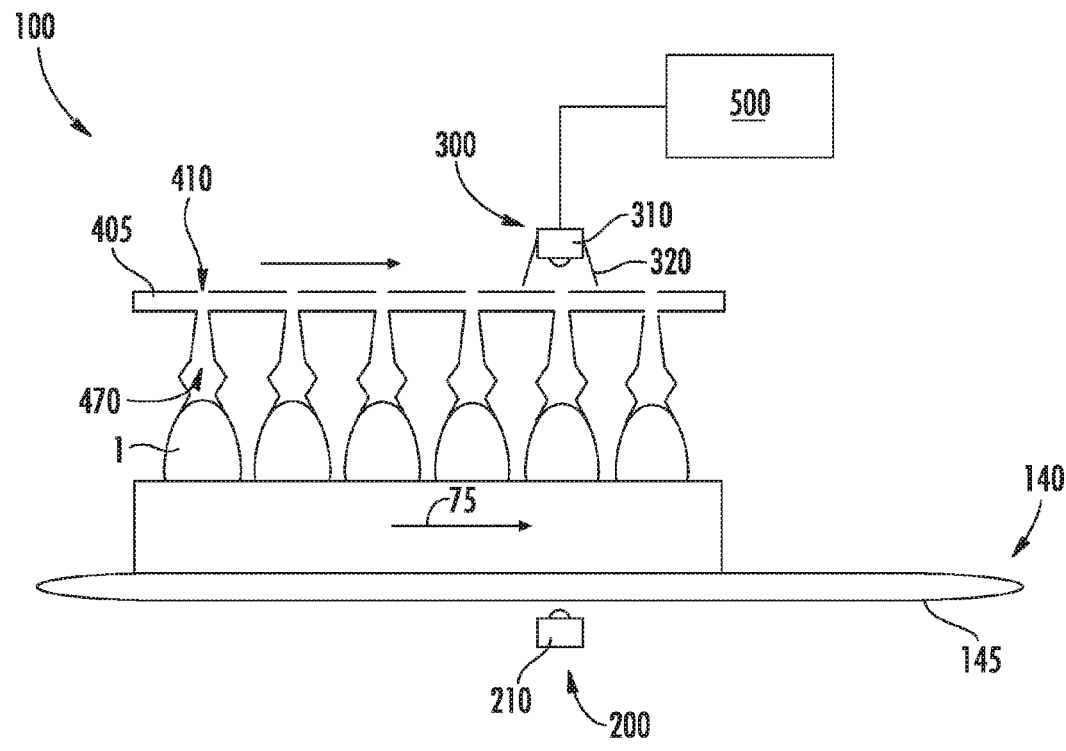
Figure 7:
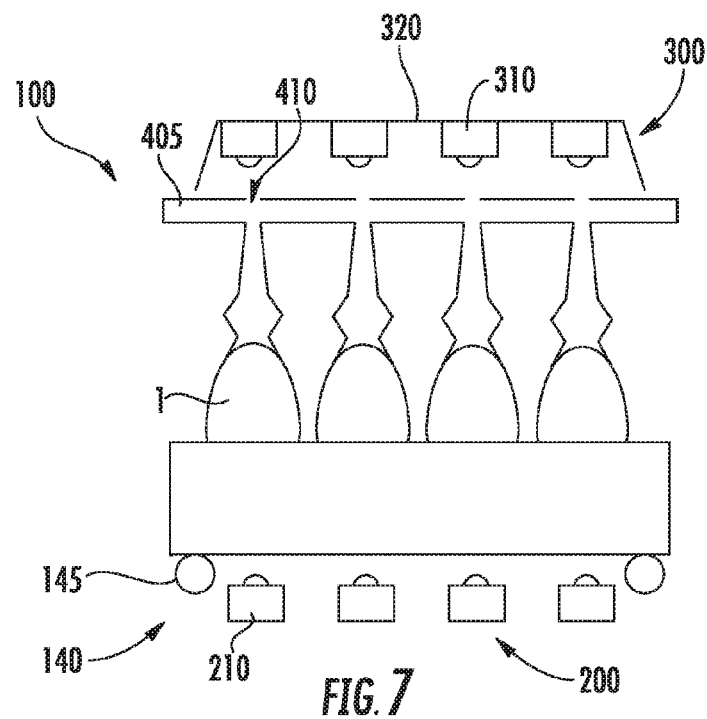
Figure 8:
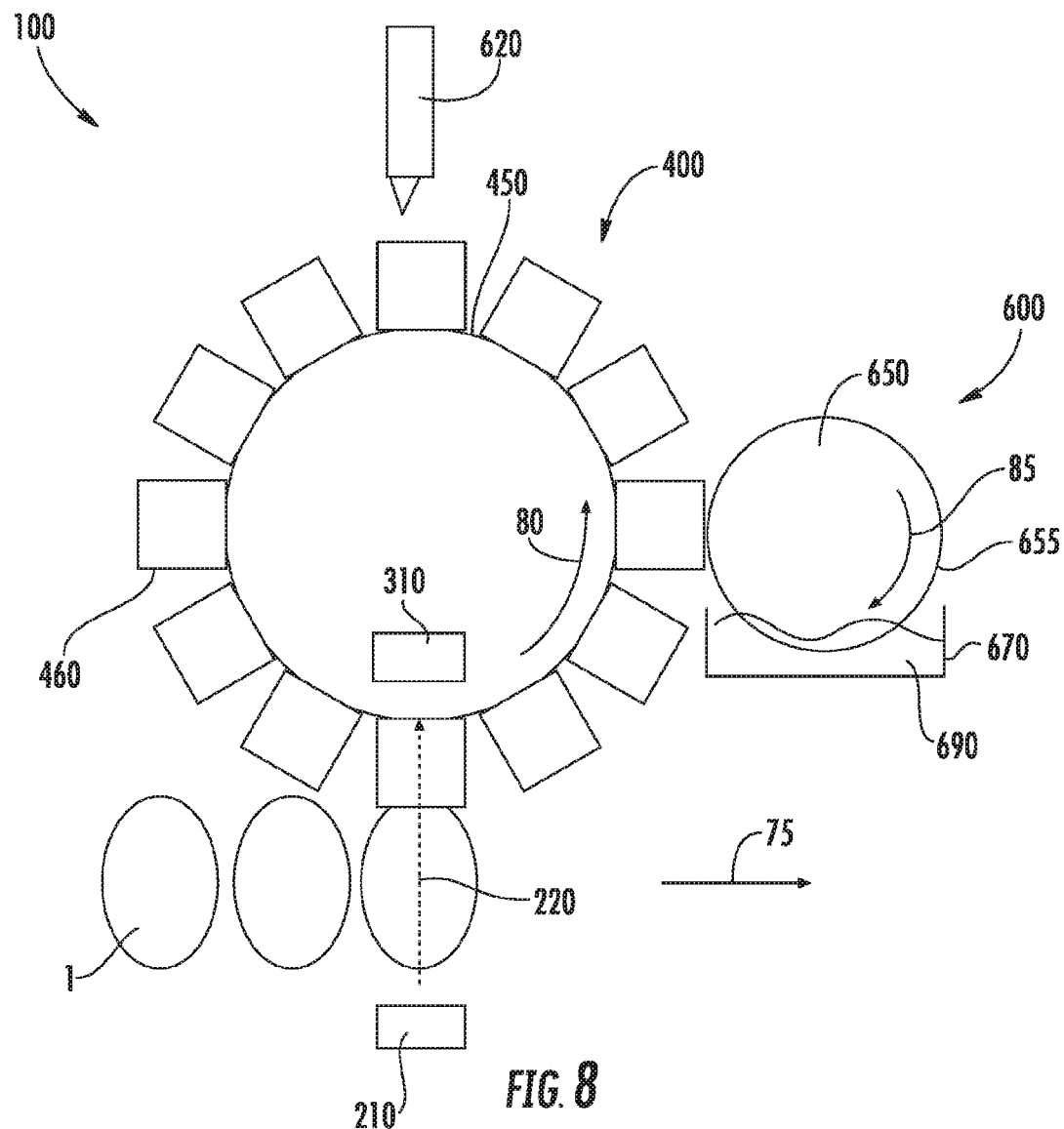

Having thus described various embodiments of the present disclosure in general terms, reference will now be made to the accompanying drawings, which are not necessarily drawn to scale, and wherein:

FIG. 1 illustrates a live chicken egg at about day one of incubation;

FIG. 2 illustrates a live chicken egg at about day eleven of incubation;

FIG. 3 is a perspective schematic view of an egg flat capable of containing eggs in a fixed position;

FIG. 4 is a side schematic view of an egg identification system interacting with an egg flat carrying a plurality of eggs, according to one aspect of the present disclosure;

FIG. 5 is a front schematic view of the egg identification system of FIG. 4;

FIG. 6 is a side schematic view of an egg identification system interacting with an egg flat carrying a plurality of eggs, according to another aspect of the present disclosure;

FIG. 7 is a front schematic view of the egg identification system of FIG. 6; and FIG. 8 is a side schematic view of an egg identification system having a cleaning assembly for cleaning an optical shielding assembly, according to one aspect of the present disclosure.

DETAILED DESCRIPTION OF THE DISCLOSURE

Various aspects of the present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

The present disclosure is directed to systems and methods for determining the viability of a plurality of eggs in a high throughput manner while improving accuracy by addressing the issues of optical aberrations and light scattering and reflectance around an egg. In this regard, the present disclosure provides a solution for improving accuracy of distinguishing viable and non-viable eggs while an egg flat carrying eggs is continuously moved along a processing line, without stopping such that data can be collected for analyzing viability. The methods and systems according to aspects of the present disclosure may be utilized for accurately identifying live and non-live eggs at any time during embryonic development (also referred to as the incubation period). Aspects of the present disclosure are not limited to identification only at a particular day (e.g., day eleven) or time period during the embryonic development period. In addition, methods and apparatus according to aspects of the present disclosure may be used with any types of avian eggs including, but not limited to, chicken, turkey, duck, geese, quail, pheasant eggs, exotic bird eggs, etc.

FIGS. 4-8 illustrate an egg identification system 100 capable of implementing various aspects of the present disclosure. The egg identification system 100 may include a frame and a conveyor system 140 configured to convey a plurality of eggs 1 contained in an egg flat 50 to an identification position. The conveyor system 140 may include one or more endless belts 145 for transporting the egg flats 50 in a processing direction 75. In some instances, the egg identification system 100 may include a display capable of displaying information related to the egg identification system and/or the eggs 1 passing therethrough. The egg identification system 100 may include a controller for controlling various aspects thereof, including the ability to enable and disable certain components of the egg identification system 100. The egg identification system 100 may be portable and, in some instances, may be configured in a modular manner such that it may be connected to other associated devices, such as, for example, an egg injection apparatus, an egg sorting apparatus, an egg transfer apparatus, an egg remover apparatus, or a gender identification apparatus. In some instances, the egg identification system 100 may be directly implemented within an egg injection apparatus, an egg sorting apparatus, an egg transfer apparatus, an egg remover apparatus, or a gender identification apparatus.

Referring to FIG. 3, the egg flat 50 may be formed of a plurality of intersecting slats 52 confined by a plurality of ends 54. The slats 52 may define a plurality of open-ended pockets 56, with each pocket 56 capable of receiving an end of a respective egg 1. In some instances, the narrow end 10 (FIGS. 1 and 2) of the egg 1 may be received within the pocket 56 such that the blunt end 20 projects above the egg flat 50.

According to some aspects, the egg identification system 100 may be configured to measure the opacity (i.e., a measurement related to the amount of light passing through an egg when illuminated by a light source) of the eggs 1 carried in the egg flat 50. The light received by a detector for measurement of a given egg may be detected in raw form as voltage data, which may then be modified, standardized, corrected or otherwise manipulated into some unit of measure (arbitrary or otherwise). As is known to those familiar with poultry eggs, although egg shells appear opaque under most lighting conditions, they are in reality somewhat translucent, and when placed in front of a direct light, such as a candle or light bulb, the contents of the egg can be observed to a certain extent. Accordingly, various candling discrimination techniques may be used for the purpose of discriminating between live eggs and non-live eggs. Live eggs include eggs that were fertilized and contain a living embryo. Non-live eggs could be infertile eggs (sometimes referred to as "clear" eggs) or eggs with dead embryos. Compared to live eggs, infertile eggs allow more light to pass therethrough (particularly as compared to live eggs at later stages of incubation/embryo development) when illuminated since an embryo is not present.

Referring now to FIGS. 4-8, the egg identification system 100 may include an emitter assembly 200 having a plurality of emitters 210, each emitter 210 being capable of emitting electromagnetic radiation (e.g., light) toward a respective egg 1 positioned proximate thereto. The emitters 210 may be configured to emit electromagnetic radiation of various wavelengths of the electromagnetic spectrum, including, for example, visible light, infrared light and near-infrared light. In some instances, each emitter 210 may be capable of illuminating the eggs 1 with two or more wavelengths of light at one end of the egg 1. In such instances, the measured opacity of the eggs 1 at various wavelengths may be used or manipulated to determine viability of the embryo. According to some aspects, the emitters 210 may be formed of a light emitting diode (LED) configured to emit light from the infrared portion of the electromagnetic spectrum. However, aspects of the present disclosure are not limited to the use of LEDs or infrared radiation. Various types of light emission sources may be utilized without limitation such as, for example, a laser diode source or a solid-state excitation source. The emitters 210 may emit light that is pulsed, time-sliced or modulated so as to avoid measurement errors caused by light emitted from adjacent emitters 210.

The egg identification system 100 may further include a detector assembly 300 having a plurality of detectors 310 for receiving electromagnetic radiation (e.g., light) transmitted through the egg 1 during the candling operation. In some instances, the detector assembly 300 may be positioned opposite the emitter assembly 200 in axial alignment so as to form a plurality of emitter-detector pairs capable of evaluating eggs 1 transported in the egg flat 50 in a high throughput manner. Each emitter 210 in the emitter assembly 200 may contain light sources at one or more wavelengths so that the associated detector 310 at each position may measure opacity at one or more wavelengths. To measure several wavelengths with a single detector 310, light from the different light sources of the emitter 210 may be time-sliced or modulated to separate the opacity measurement at each wavelength.

In operation, the emitter-detector pairs may be arranged in an array and utilized to classify a respective array of eggs 1 supported by the egg flat 50. Each detector 310 may include photodetection means for detecting and carrying out photoelectric conversion of the light transmitted through the egg 1. For example, each detector 310 may employ a sensor such as, for example, a photodetector (e.g., a PIN diode) for generating an output signal corresponding to the intensity of the light leaving an egg 1. The sensor may be any type of sensor capable of detecting the wavelength(s) of light emitted by the emitter 210 at modulation frequencies, including DC. The detectors 310 may be disposed within a detector assembly housing 320. Multiple detectors 310 may be located at each egg position to measure opacity at multiple wavelengths. According to one aspect, there may be multiple emitters 210 and a single detector 310 at each position.

In some instances, the egg identification system 100 may implement the emitter-detector pairs through which the eggs pass such that an opacity measurement may be determined, as disclosed in U.S. Pat. No. 5,900,929 to Hebrank et al., which is incorporated herein in its entirety. In some instances, the emitter assembly 200 may be positioned above the conveyed egg flats 50 and the detector assembly 300 positioned below the conveyed egg flats 50. In operation, once an egg 1 is disposed between the emitter-detector pair, the emitter 210 may emit light (indicated as 220 in FIG. 8) into the egg 1. The detector 310 may receive light that leaves or is transmitted through the egg 1 and may generate an output signal corresponding to the intensity of the light leaving the egg 1. A processor 500 may be in communication with the detector assembly 300 and configured to process output signals from the detectors 310 to determine the viability of the egg 1. Viability may be determined by processing the output signal in various manners.

In order to reduce light scattering and optical aberrations affecting the output signal, the egg identification system 100 may include an optical shielding assembly 400. The optical shielding assembly 400 may be configured to move with respect to the emitters 210 and/or the detectors 310 so as to provide optical shielding thereto. In this manner, the opacity of the eggs 1 may be measured on continuously moving egg flats 50 to achieve desired throughput. That is, live eggs may be discriminated from non-live eggs in moving egg flats 50 by illuminating each egg 1 with wavelengths of light at one end of the egg, measuring the light passing through the other side of the eggs, and positioning a motion compatible optical shielding at one or both ends of the egg 1 to block light that could illuminate the detectors 310 without passing through the egg 1. The movable optical shielding assembly 400 seeks to improve accuracy of live/non-live discrimination. With the movable optical shielding assembly 400, opacity measurements may be made for all eggs in a row of the egg flat 50 in less than 0.01 seconds, thereby allowing the egg flats 50 to continuously move at speeds of about 10 to 20 inches per second (about 25-50 centimeters per second). At such speeds, a detector assembly 300 of one row of detectors 310 may be capable of processing over 100,000 to 200,000 eggs per hour.

According to one aspect, measurement of egg opacity may occur by emitting electromagnetic radiation at one or more wavelengths using the emitter assembly 200 (e.g., light source) on one side or end of the eggs, positioning the detector assembly 300 on the other side or end, and placing optical shielding assembly 400 that blocks light which might propagate from the emitter assembly 200 to the detector assembly 300 without passing through the egg 1. The optical shielding assembly 400 may move in alignment with the eggs 1 on the moving egg flat 50 so that only a single row of opacity measurements are needed (i.e., using a single row of emitter-detector pairs, where in some instances each emitter 210 may emit light at one or multiple wavelengths).

In some instances, the emitters 210 and/or the detectors 310 are fixedly positioned with respect to the optical shielding assembly 400. In this regard, the emitters 210 and/or the detectors 310 are stationary while the optical shielding assembly 400 is configured to move. The optical shielding assembly 400 may be positioned to move about the emitters 210, the detectors 310, or both. In some instances, multiple optical shielding assemblies 400 may be implemented such that a respective optical shielding assembly 400 is positioned proximate to the emitter assembly 200 and the detector assembly 300 such that both ends of the eggs 1 are subjected to optical shielding. It is also noted that while the illustrated aspects of the present disclosure show the emitter assembly 200 below the egg flat 50 and the detector assembly 300 above the egg flat 50, the orientation could be reversed such that the detector assembly 300 is positioned above the egg flat 50 and the emitter assembly 200 positioned below the egg flat 50.

With reference to FIGS. 4 and 5, according to one aspect of the present disclosure, the optical shielding assembly 400 may be positioned above the conveyor system 140 such that the optical shielding is applied to the upward end of the eggs 1. The optical shielding assembly 400 may include a rotatable drum 450 and a plurality of optical shields 460 extending radially from the rotatable drum 450. As the drum 450 rotates, the optical shields 460 become positioned over the eggs 1 as the opacity measurement is made using the emitter-detector pairs. The optical shields 460 may continuously move into proximity of the eggs 1 during rotation so as to provide optical shielding during detection of the electromagnetic radiation. Rotation of the drum 450 may be synchronized with the motion of the egg flats 50 along the processing direction 75 so that a direct light path exists from the egg 1 to the detector 310 (or emitter 210) when the egg is directly under the drum 450. In some instances, the detectors 310 may be disposed within the drum 450 and fixedly positioned with respect to the drum 450 such that the detectors 310 remain stationary as the drum 450 rotates thereabout. In this regard, the drum 450 may provide optical shielding to the detectors 310 against ambient light. The drum 450 may rotate in a rotational direction 80 such that, as the optical shields 460 come into contact with the eggs 1, the optical shields 460 are also moving substantially in the same direction as the processing direction 75.

In instances where the optical shielding assembly 400 is used in conjunction with the emitter assembly 200, the emitters 210 may be fixedly positioned with respect to the movable optical shielding assembly 400 such that the emitters 210 remain stationary as the optical shielding assembly 400 rotates thereabout. In addition, the detectors 310 (and/or emitters 210) may be connected to the drum 450 so as to rotate therewith and be coupled in a one-to-one relationship with the optical shields 460, but such a configuration would implement more than a single row of detectors 310 (or emitters 210).

In some instances, the optical shields 460 may be in the form of open-ended enclosures defining an optical chamber 470. The optical shields 460 may be opaque so as to provide the desired optical shielding. The optical shields 460 may be constructed from a compliant, flexible, or resilient material that is capable of self-adjusting to provide good contact with the eggs 1. The optical shields 460 may also be constructed from a rigid material. In some instances, it may be desirable to form a mechanical seal with the eggs 1 when the optical shields 460 come into contact therewith. In other instances, it may be desirable no to contact the eggs with the optical shields 460. In such instances, the optical shields 460 may be lightly pressurized such that the optical shields 460 maintain a small slot or skirt of air between the optical shields 460 and the eggs 1, thereby allowing the pressure to float the optical shield 460 just above the egg surface to minimize contact. The optical shields 460 may be configured to allow line-of-sight from the emitter 210 to the detector 310 in an emitter-detector pair.

According to other aspects of the present disclosure, as shown in FIGS. 6 and 7, another form of the optical shielding assembly 400 may be a plate 405 positioned above the conveyor system 140 and configured to move laterally with the eggs 1 and egg flat 50 along the processing direction 75. The plate may include apertures 410 (about 0.5 to 1.0 cm in diameter) centered over each egg 1. The egg flat 50 and the plate 405 may pass through a row of emitter-detector pairs that measure the opacity of each egg 1 as the associated row of apertures 410 passes over it. The plate 405 may be opaque (e.g., black) so as to both absorb and block light that might scatter from the emitter 210 to the detector 310 associated with each egg 1. The plate 405 may sit slightly above the tallest egg or may carry compliant optical shields 460 for complete optical isolation of the egg shell from ambient light. The plate 405 may be carried on rails above and moved with the egg flat 50 either by a mechanical attachment to the egg flat 50 or by an external actuator like a lead screw or belt drive. Thus, the plate 405 lets a single row of emitter-detector pairs measure all eggs 1 on an egg flat 50 using the plate 405 and optical shields 460 that move with the egg flat 50. The plate 405 may be rigid or a lightweight foam and plastic structure with integral or attached optical shields 460. In some instances, an additional plate 405 may be used below the egg flat 50 to provide optical shielding to the emitters 210. The plate 405 may be moved from each egg flat 50 exiting the egg identification system 100 back to the next egg flat 50 entering the egg identification system 100.

With reference to FIG. 8, in some instances, a cleaning assembly 600 may be provide for cleaning the optical shielding assembly 400, and more particularly for cleaning the optical shields 460 so as to reduce cross-contamination of eggs 1 coming into contact with the optical shields 460. According to one aspect, the cleaning assembly 600 may include a cleaning drum 650 capable of rotating through a fluid bath in which a container 670 holds a cleaning fluid 690 such as a sanitation fluid. As an external surface 655 of the cleaning drum 650 passes through the fluid bath, the external surface 655 carries cleaning fluid 690 with it such that it can contact the optical shields 460 to apply cleaning fluid thereto. In some instances, the cleaning drum 650 may be rotated in a rotational direction 85 opposite that of the drum 450. As shown in FIG. 8, the cleaning drum 650 may be rotated clockwise while the drum 450 is rotated counter-clockwise. In some instances, an air knife 620 may be provided to provide pressurized air to the optical shields 460 in order to remove any excess egg fluid/debris or cleaning fluid 690 therefrom.

Many modifications and other aspects of the present disclosure set forth herein will come to mind to one skilled in the art to which this disclosure pertains having the benefit of the teachings presented in the foregoing descriptions and the associated drawings. For example, it is noted that a single mechanism may be configured to move both the egg flat 50 and the plate 405 past the emitter-detector pairs. Therefore, it is to be understood that the present disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. An egg identification system, comprising:
   an emitter assembly configured to emit electromagnetic radiation toward a plurality of eggs positioned proximate thereto;
   a detector assembly positioned proximate to the emitter assembly, the detector assembly having a plurality of detectors fixedly positioned with respect to the emitter assembly and configured to detect electromagnetic radiation transmitted through the eggs;

a conveyor system configured to transport the eggs in an egg flat in a processing direction to an identification position between the emitter assembly and the detector assembly;

an optical shielding assembly configured to move with respect to the detectors and to provide optical shielding for detection of the electromagnetic radiation transmitted through the eggs;

a processor in communication with detector assembly and configured to determine viability of the eggs using the detected electromagnetic radiation; and wherein the optical shielding assembly is configured to move laterally with the eggs along the processing direction.

2. A system according to claim 1, wherein the detector assembly and the conveyor system are synchronized such that the eggs are analyzed for viability while the egg flat is continuously moved along the conveyor system.

3. A system according to claim 1, further comprising a cleaning assembly configured to interact with the optical shielding assembly for cleaning thereof.

4. A system according to claim 1, wherein the detectors are configured to generate an output signal corresponding to intensity of electromagnetic radiation from the emitter assembly transmitted through a respective egg.

5. A method of classifying an egg, the method comprising:

conveying a plurality of eggs through an egg identification system with a conveyor system in a processing direction to an identification position between an emitter assembly and a detector assembly of the egg identification system, the detector assembly having a plurality of detectors fixedly positioned with respect to the emitter assembly and configured to detect electromagnetic radiation transmitted through the eggs;

emitting electromagnetic radiation via the emitter assembly toward the eggs;

moving an optical shielding assembly laterally with the eggs along the processing direction and in relation to the detectors so as to provide optical shielding for detection of the electromagnetic radiation transmitted through the eggs;

detecting electromagnetic radiation transmitted through the eggs with the detectors; and generating an output signal corresponding to intensity of electromagnetic radiation from the emitter assembly transmitted through a respective egg.

6. A method according to claim 5, further comprising synchronizing the detector assembly and the conveyor system such that the eggs are analyzed for viability while the egg flat is continuously moved along the conveyor system.

7. A method according to claim 5, further comprising automatically cleaning with a cleaning assembly the optical shielding assembly.

8. A method according to claim 5, further comprising determining with a processor egg viability using the detected electromagnetic radiation.

* * * * *